(12) United States Patent
Takahata et al.

(10) Patent No.: US 7,971,425 B2
(45) Date of Patent: Jul. 5, 2011

(54) UREA CONCENTRATION IDENTIFYING SYSTEM, METHOD FOR INDENTIFYING UREA CONCENTRATION AND AUTOMOBILE EXHAUST GAS REDUCING SYSTEM USING SAME, AND METHOD FOR REDUCING AUTOMOBILE EXHAUST GAS

(75) Inventors: Takayuki Takahata, Ageo (JP); Toshiaki Kawanishi, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 1458 days.

(21) Appl. No.: 10/527,255

(22) PCT Filed: Sep. 10, 2003

(86) PCT No.: PCT/JP03/11568
§ 371 (c)(1),
(2), (4) Date: Mar. 9, 2005

(87) PCT Pub. No.: WO2004/025286
PCT Pub. Date: Mar. 25, 2004

(65) Prior Publication Data
US 2006/0026949 A1 Feb. 9, 2006

(30) Foreign Application Priority Data
Sep. 10, 2002 (JP) .................. 2002-264603

(51) Int. Cl.
*F01N 3/00* (2006.01)

(52) U.S. Cl. ......... 60/276; 60/299; 204/403.1; 204/408; 324/439; 324/446

(58) Field of Classification Search .............. 60/274, 60/276, 299; 204/403.1, 408; 324/439, 446; 436/149–151, 155
See application file for complete search history.

(56) References Cited

U.S. PATENT DOCUMENTS

| | | | | |
|---|---|---|---|---|
| 5,546,004 A | * | 8/1996 | Schmelz | 324/446 |
| 6,114,176 A | * | 9/2000 | Edgson et al. | 436/108 |
| 6,681,624 B2 | | 1/2004 | Furuki et al. | |
| 6,787,047 B1 | * | 9/2004 | Hahn et al. | 216/2 |
| 6,920,399 B2 | * | 7/2005 | Priev et al. | 702/23 |
| 7,153,693 B2 | * | 12/2006 | Tajiri et al. | 436/108 |
| 7,722,813 B2 | * | 5/2010 | Inoue et al. | 422/68.1 |
| 2006/0119277 A1 | * | 6/2006 | Ito et al. | 315/106 |
| 2008/0205478 A1 | * | 8/2008 | Sasanuma et al. | 374/44 |

FOREIGN PATENT DOCUMENTS

| | | |
|---|---|---|
| JP | 3-262949 A | 11/1991 |
| JP | 11-153561 A | 6/1999 |
| JP | 2001-20724 A | 1/2001 |
| WO | WO 01/44761 A | 6/2001 |

* cited by examiner

*Primary Examiner* — Tu M Nguyen
(74) *Attorney, Agent, or Firm* — The Webb Law Firm

(57) ABSTRACT

The concentration of the urea of a urea solution is identified accurately and immediately. A pulse voltage is applied for a predetermined time to a urea concentration identifying sensor heater including a heater and an identifying liquid temperature sensor provided in the vicinity of the heater, a urea solution to be identified is heated by the heater, and the concentration of the urea is identified with a voltage output difference V0 corresponding to a temperature difference between an initial temperature and a peak temperature in the identifying liquid temperature sensor.

28 Claims, 13 Drawing Sheets

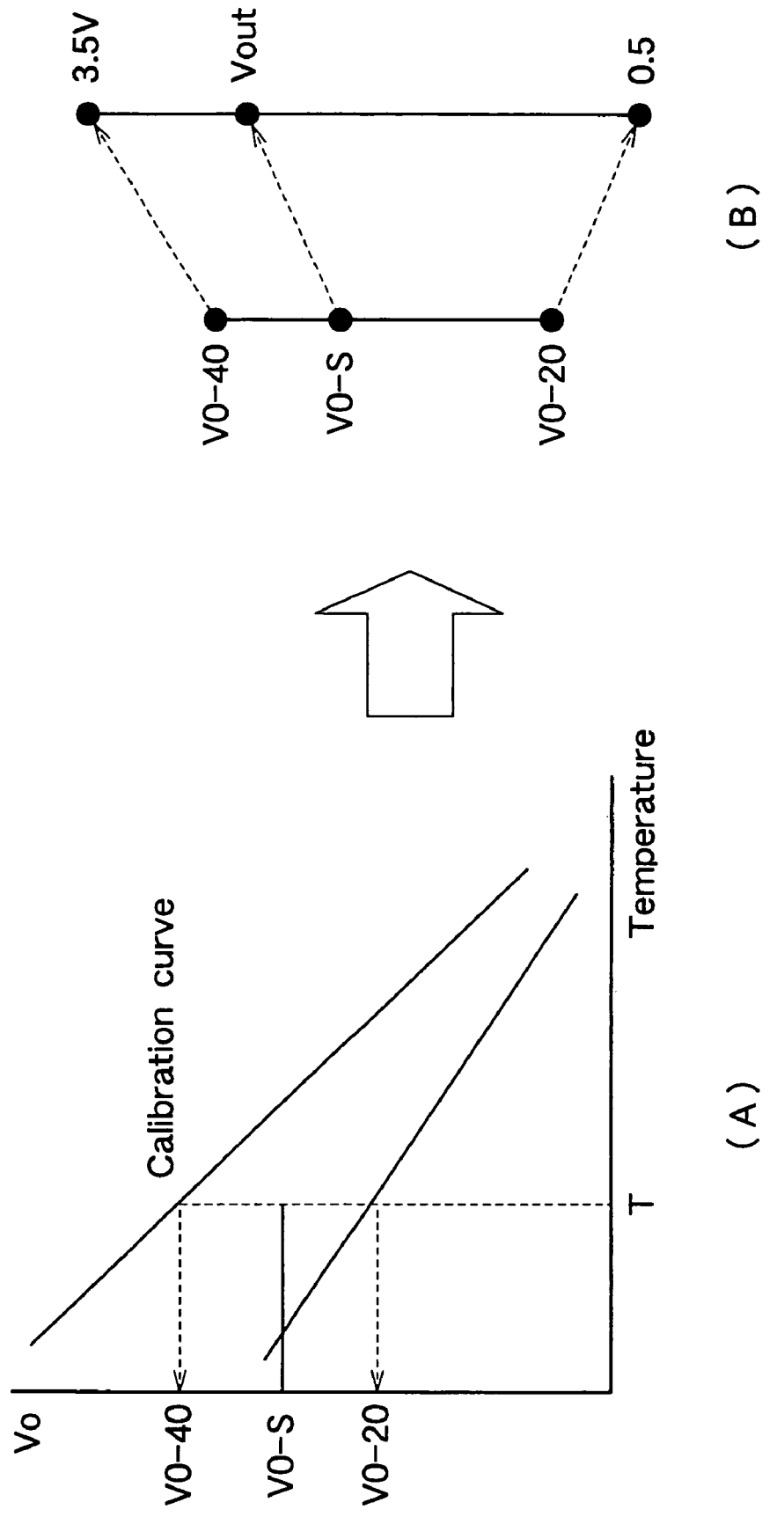

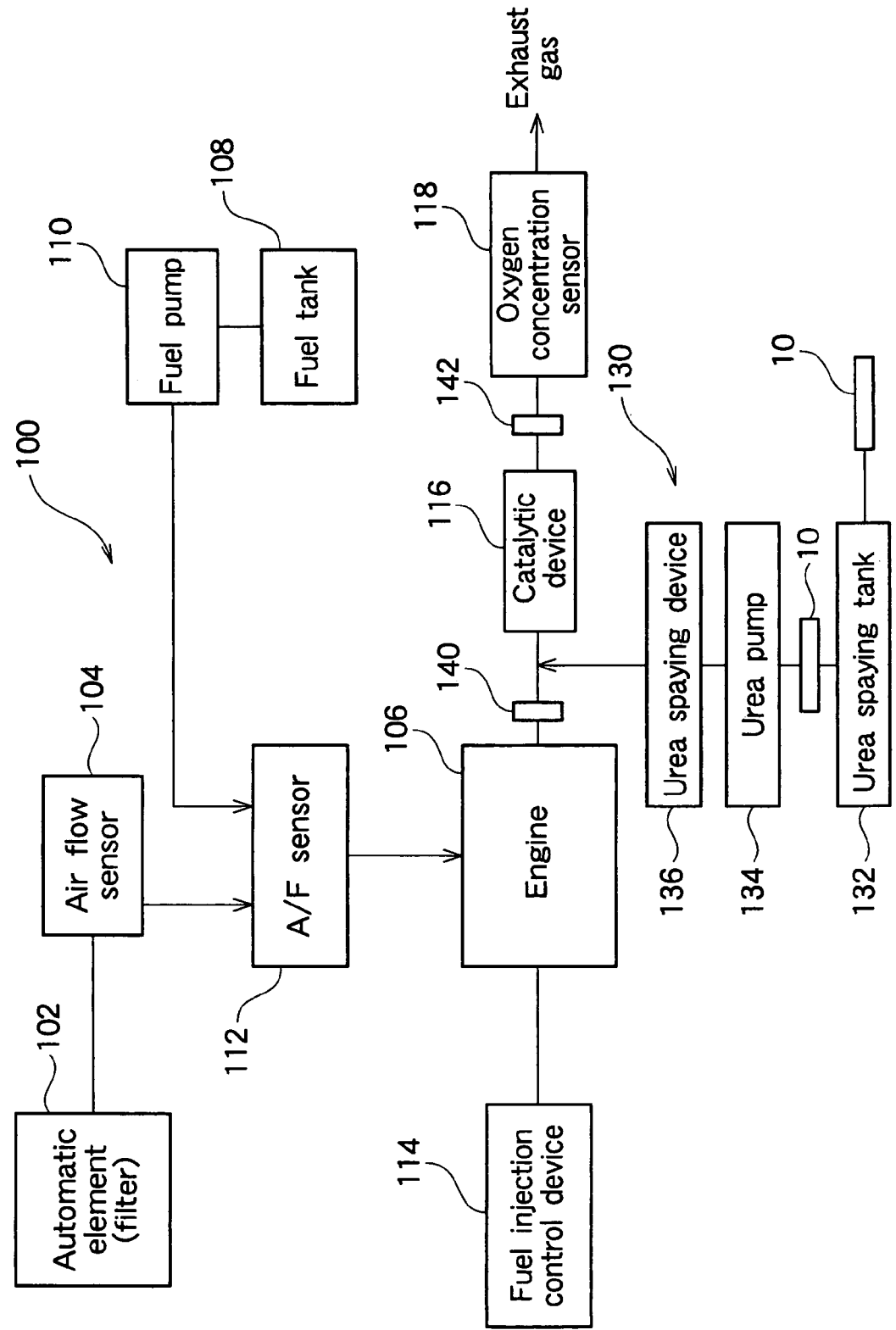

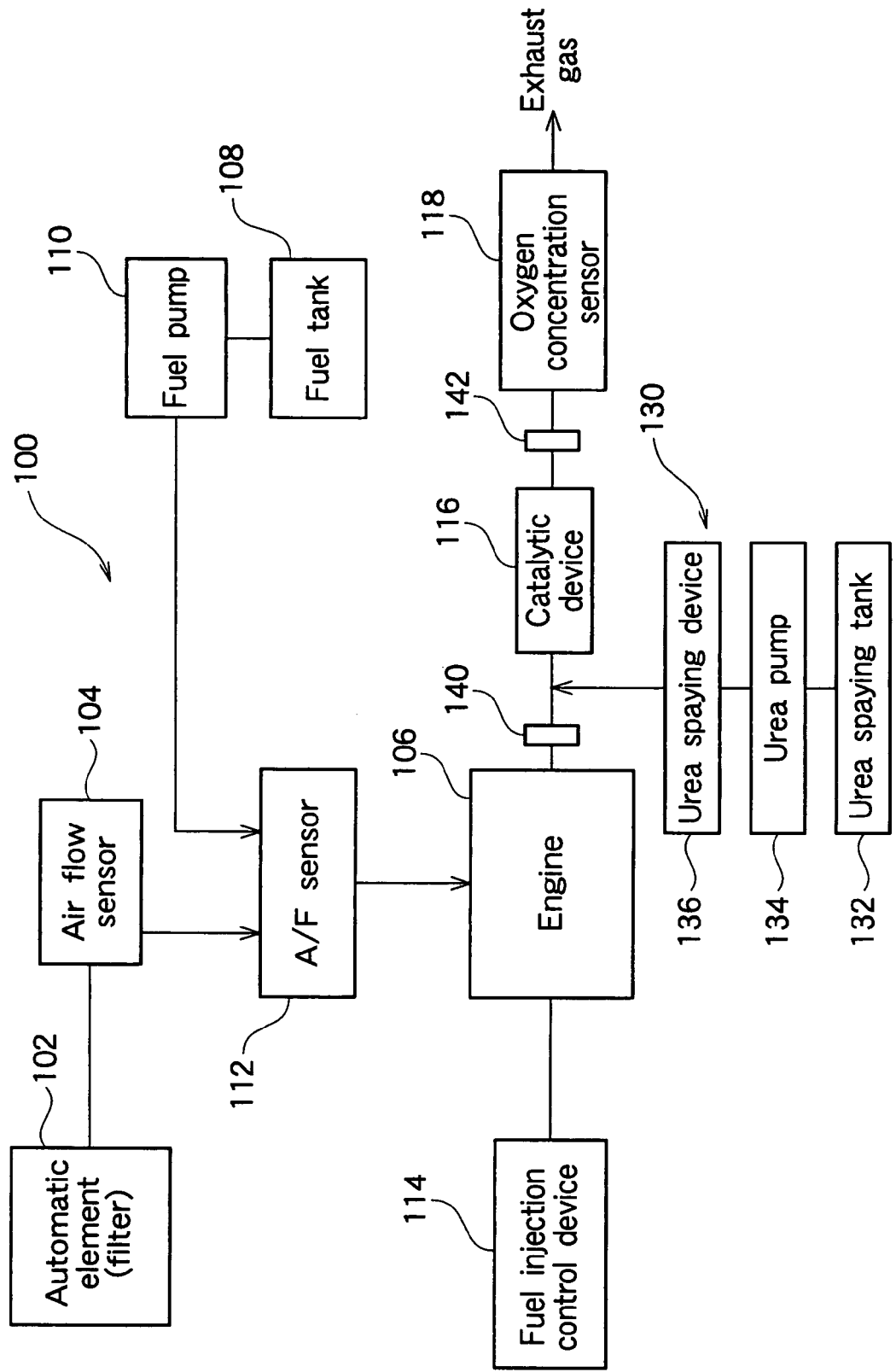

UREA CONCENTRATION IDENTIFYING SYSTEM, METHOD FOR INDENTIFYING UREA CONCENTRATION AND AUTOMOBILE EXHAUST GAS REDUCING SYSTEM USING SAME, AND METHOD FOR REDUCING AUTOMOBILE EXHAUST GAS

TECHNICAL FIELD

The present invention relates to an apparatus and method for identifying the concentration of the urea of a urea solution, and an apparatus and method for reducing the exhaust gas of a car using the apparatus and method.

BACKGROUND ART

Conventionally, the exhaust gas of a car contains pollutants such as unburned hydrocarbon (HC), an NOx gas and an SOx gas. In order to reduce the pollutants, therefore, Sulfur (S) in a gasoline or light oil is removed for the Sox or unburned Hydrocarbon (HC) is burned by a catalyst, for example.

More specifically, as shown in FIG. 13, a car system 100 takes air in through an automatic element (filter) 102 and feeds the air into an engine 106 through an airflow sensor 104. Moreover, the car system 100 feeds a fuel in a fuel tank 108 into the engine 106 through a fuel pump 110.

Based on the result of the detection of an A/F sensor 112, the injection of the fuel in the engine 106 is controlled by a fuel injection control device 114 in order to have a predetermined theoretical air fuel ratio.

For an exhaust gas fed from the engine 106, hydrocarbon (HC) in the exhaust gas is burned by a catalytic device 116 and is then discharged as the exhaust gas through an oxygen concentration sensor 118.

In consideration of the influence of the NOx in the exhaust gas on an environment, recently, there has been proposed a method of supplying a urea solution to the catalytic device 116, thereby reducing the NOx to be non-toxic as an $N_2$ gas in order to decrease the NOx in the exhaust gas discharged from the fuel of a car, for example, a gasoline or light oil.

More specifically, as shown in FIG. 13, the car system 100 has such a structure as to supply a urea solution to the upstream side of the catalytic device 116 through a urea solution supplying mechanism 130 constituted by a urea solution tank 132 for storing a urea solution, a urea pump 134 and a urea spraying device 136 for spraying the urea solution fed from the urea pump 134 onto the upstream side of the catalytic device 116.

In such a car system, it is suitable that 32.5% by weight of urea and 67.5% by weight of $H_2O$ should be set in order to efficiently generate a reducing reaction at the upstream side of the catalytic device 116 without causing the urea solution to cake, for example.

For this reason, conventionally, NOx sensors 140 and 142 have been provided at the upstream and downstream sides of the catalytic device 116 respectively to measure the concentration of NOx in order to decide whether or not the concentration of a urea sprayed onto the upstream side of the catalytic device 116 is constant.

However, the NOx sensors 140 and 142 measure the concentration of the urea as a result of the reducing rate of NOx. For this reason, it is impossible to previously identify the concentration of the urea which is contained in the urea solution tank 132 or is sprayed. Moreover, the NOx sensors 140 and 142 do not have very high sensitivities.

The present inventors have already proposed a fluid identifying method in Japanese Laid-Open Patent Publication No. 11-153561 (particularly see paragraphs [0042] to [0049]). This method is to cause a heating member to generate heat by carrying electricity, heating a temperature detector through the heat generation, thermally influencing a heat transfer from the heating member to the temperature detector through a fluid to be identified, and distinguishing the type of the identified fluid based on an electrical output corresponding to the electric resistance of the temperature detector, thereby periodically carrying the electricity to the heating member.

In the fluid identifying method, however, it is necessary to periodically carry the electricity to the heating member (in a multipulse). For this reason, a long time is required for the identification so that it is hard to identify a fluid instantaneously. In this method, moreover, it is possible to identify a fluid based on a central value for substances having very different properties such as water, air and oil. However, it is hard to identify the concentration of the urea of the urea solution accurately and immediately.

In consideration of such circumstances, it is an object of the present invention to provide an apparatus and method for identifying the concentration of the urea of a urea solution which can identify the concentration of the urea of the urea solution accurately and immediately.

Moreover, it is an object of the present invention to provide an apparatus and method for reducing the exhaust gas of a car using the apparatus and method for identifying the concentration of the urea of a urea solution which can efficiently reduce the exhaust gas and can enhance a mileage.

SUMMARY OF THE INVENTION

The present invention has been made to solve the problems and to attain the objects in the prior art described above, and provides an apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and the apparatus further comprising an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor.

Moreover, the present invention provides a method for identifying a concentration of a urea of a urea solution, comprising the steps of:

applying a pulse voltage for a predetermined time to a urea concentration identifying sensor heater including a heater and an identifying liquid temperature sensor provided in the vicinity of the heater;

heating an identified urea solution by the heater; and identifying the concentration of the urea with a voltage output difference V0 corresponding to a temperature difference between an initial temperature and a peak temperature in the identifying liquid temperature sensor.

By such a structure, it is sufficient that the pulse voltage is applied for the predetermined time. Consequently, it is possible to identify the concentration of the urea of the urea solution accurately and immediately through heating for a short time.

More specifically, there are utilized the correlation of the kinetic viscosity of the urea solution with a sensor output, a natural convection, and furthermore, an applied voltage having one pulse. Therefore, it is possible to identify the concentration of the urea of the urea solution accurately and immediately.

Furthermore, the present invention is characterized in that the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0=V2-V1.$$

By such a structure, it is possible to accurately obtain the voltage output difference V0 based on the average value of the sampling at the predetermined number of times for the applied voltage having one pulse. Consequently, it is possible to identify the concentration of the urea of the urea solution accurately and immediately.

In addition, the present invention provides the apparatus for identifying a concentration of a urea of a-urea solution, wherein the identification control portion identifies a concentration of a urea of a urea solution with the voltage output difference V0 obtained for the identified urea solution based on calibration curve data to be a correlation of a voltage output difference with a temperature for a predetermined reference urea solution prestored in the identification control portion.

Moreover, the present invention provides the method for identifying a concentration of a urea of a urea solution, wherein a concentration of a urea of a urea solution is identified with the voltage output difference V0 obtained for the identified urea solution based on calibration curve data to be a correlation of a voltage output difference with a temperature for a predetermined reference urea solution which is prestored.

By such a structure, the concentration of the urea of the urea solution is identified with the voltage output difference V0 obtained for the identified urea solution based on the calibration curve data, which is correlated with the voltage output difference with the temperature for the predetermined reference urea solution which is prestored. Therefore, it is possible to identify the concentration of the urea of the urea solution more accurately and immediately.

Furthermore, the present invention provides the apparatus for identifying a concentration of a urea of a urea solution, wherein the identification control portion correlates a liquid type voltage output Vout for the voltage output difference V0 at a measuring temperature of the identified urea solution with an output voltage for a voltage output difference at a measuring temperature for a predetermined threshold reference urea solution and thus carries out a correction.

In addition, the present invention provides the method for identifying a concentration of a urea of a urea solution, wherein a liquid type voltage output Vout for the voltage output difference V0 at a measuring temperature of the identified urea solution is correlated with an output voltage for a voltage output difference at a measuring temperature for a predetermined threshold reference urea solution and is thus corrected.

By such a structure, the liquid type voltage output Vout for the voltage output difference V0 at the measuring temperature of the identified urea solution is correlated with the output voltage for the voltage output difference at the measuring temperature for the predetermined threshold reference urea solution and is thus corrected. Consequently, it is possible to eliminate the influence of the temperature on the voltage output difference V0, thereby giving the correlation of the liquid type voltage output Vout with the properties of the urea solution more accurately. Thus, it is possible to identify the concentration of the urea of the urea solution further accurately and immediately.

Moreover, the present invention is characterized in that the urea concentration identifying sensor heater is a laminated urea concentration identifying sensor heater in which a heater and an identifying liquid temperature sensor are laminated through an insulating layer.

By such a structure, a mechanism portion for carrying out a mechanical operation is not present. Therefore, an operation failure is not caused by a deterioration with the passage of time, foreign matter in the urea solution or the like. Thus, it is possible to identify the concentration of the urea of the urea solution accurately and immediately.

In addition, the sensor portion can be constituted to be very small-sized. Consequently, it is possible to identify the concentration of the urea of the urea solution accurately with a very excellent thermal responsiveness.

Furthermore, the present invention is characterized in that the heater and the identifying liquid temperature sensor in the urea concentration identifying sensor heater are constituted to come in contact with the identified urea solution through a metallic fin, respectively.

By such a structure, the heater and the identifying liquid temperature sensor in the urea concentration identifying sensor heater do not directly come in contact with the identified urea solution. Therefore, an operation failure is not caused by a deterioration with the passage of time, foreign matters in the urea solution or the like. Thus, it is possible to identify the concentration of the urea of the urea solution accurately and immediately.

Moreover, the present invention is characterized in that the liquid temperature sensor is constituted to come in contact with the identified urea solution through the metallic fin.

By such a structure, the liquid temperature sensor does not directly come in contact with the identified urea solution. Therefore, an operation failure is not caused by, a deterioration with the passage of time, foreign matters in the urea solution or the like. Thus, it is possible to identify the concentration of the urea of the urea solution accurately and immediately.

In addition, the present invention provides an apparatus for reducing an exhaust gas of a car, comprising a urea solution supplying mechanism for supplying a urea solution to an upstream side of a catalytic device, wherein the urea solution supplying mechanism is constituted by a urea solution tank for storing the urea solution, a urea pump and a urea spraying device for spraying the urea solution fed from the urea pump to the upstream side of the catalytic device, and any of the apparatuses for identifying a concentration of a urea of a urea solution described above is provided in the urea tank or on an upstream side or a downstream side of the urea pump.

Furthermore, the present invention provides a method for reducing an exhaust gas of a car, comprising the steps of supplying a urea solution to an upstream side of a catalytic device through a urea solution supplying mechanism constituted by a urea solution tank for storing the urea solution, a urea pump and a urea spraying device for spraying the urea solution fed from the urea pump onto the upstream side of the catalytic device, and identifying a concentration of a urea of the urea solution in the urea tank or on an upstream side or a downstream side of the urea pump by using any of the methods for identifying a concentration of a urea of a urea solution described above.

By such a structure, it enables to accurately and immediately decide the amount of urea concentration, for example, whether or not 32.5% by weight of urea and 67.5% by weight of $H_2O$ are set in order to efficiently generate a reducing reaction at the upstream side of the catalytic device 116 without causing the urea solution to cake.

Accordingly, the urea of the urea solution in the urea tank can be maintained to have a predetermined concentration. Consequently, NOx in the exhaust gas can be greatly decreased by a reduction.

BRIEF DESCRIPTION OF THE DRAWINGS

FIG. 11 is a graph showing an output correcting method in the method for identifying the concentration of a urea using the apparatus for identifying the concentration of the urea of a urea solution according to the present invention, FIG. 12 is the same schematic diagram as FIG. 13, illustrating an example in which an apparatus 10 for identifying the concentration of the urea of a urea solution according to the present invention is applied to a car system, and FIG. 13 is a schematic diagram showing a conventional car system.

DETAILED DESCRIPTION OF THE INVENTION

Embodiments (examples) of the present invention will be described below in more detail with reference to the drawings.

Figure 1:
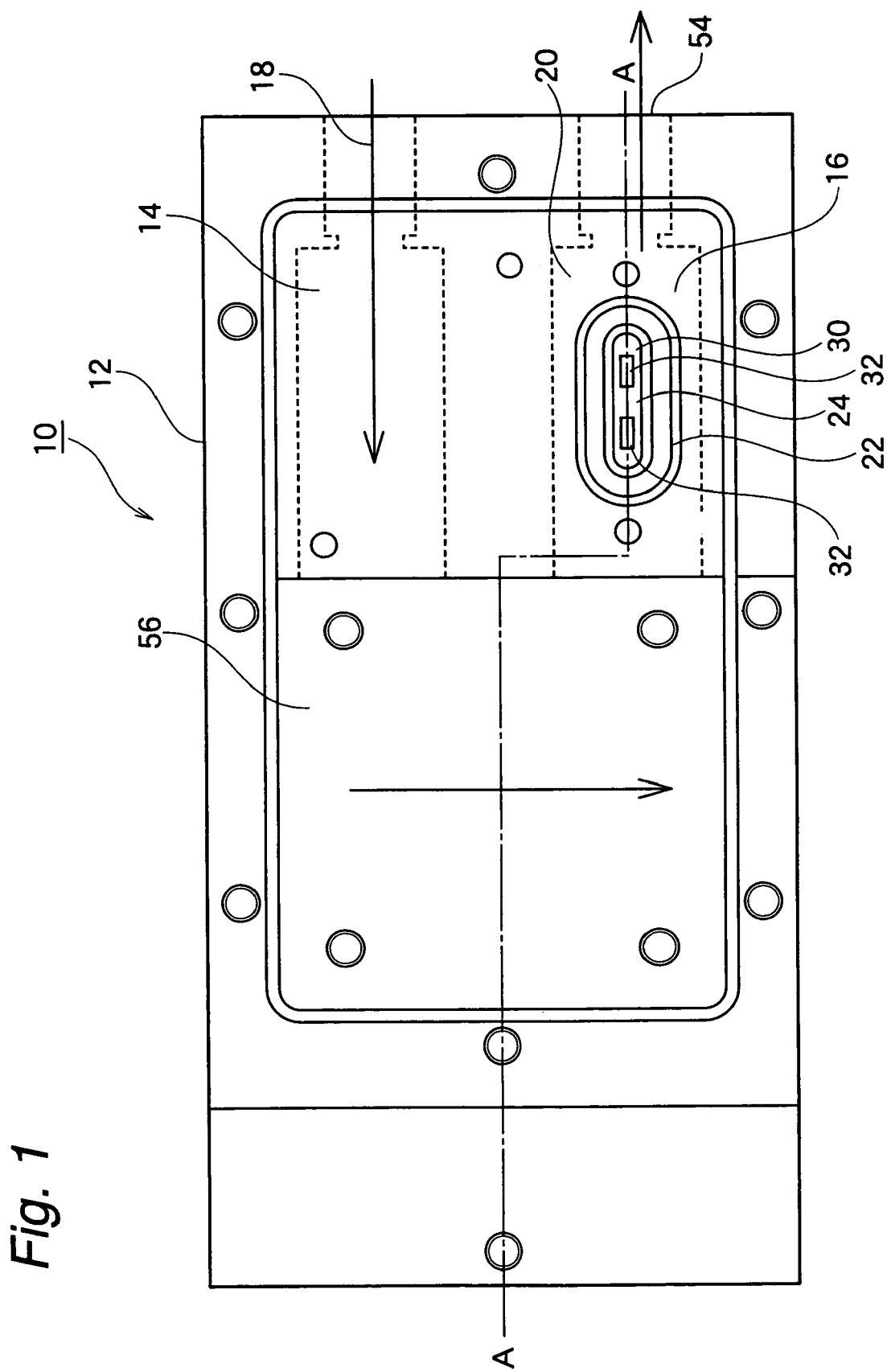
FIG. 1 is a schematic top view showing an example of an apparatus for identifying the concentration of the urea of a urea solution according to the present invention.
Figure 2:
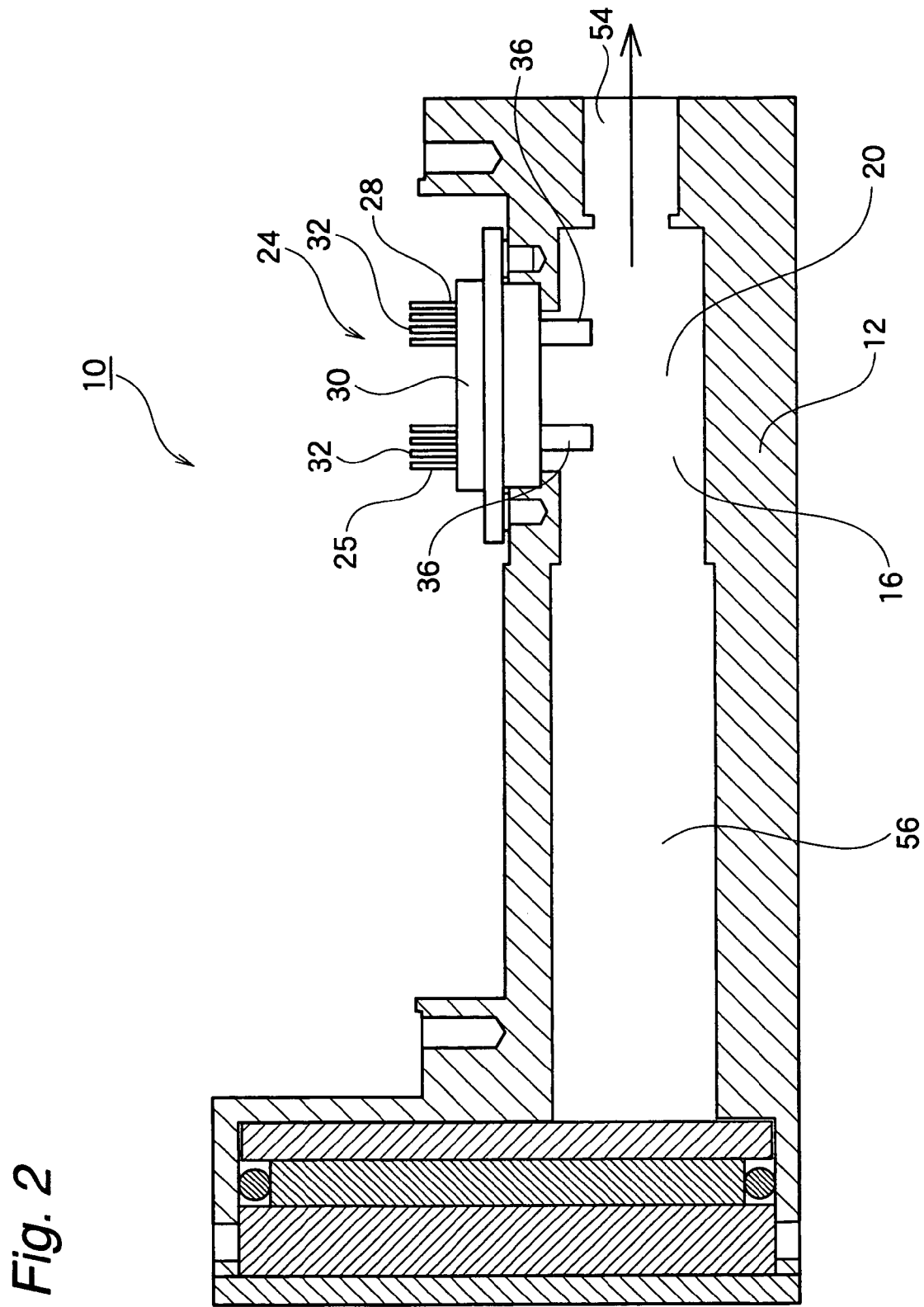
FIG. 2 is a sectional view taken along an A-A line in FIG. 1.
Figure 3:
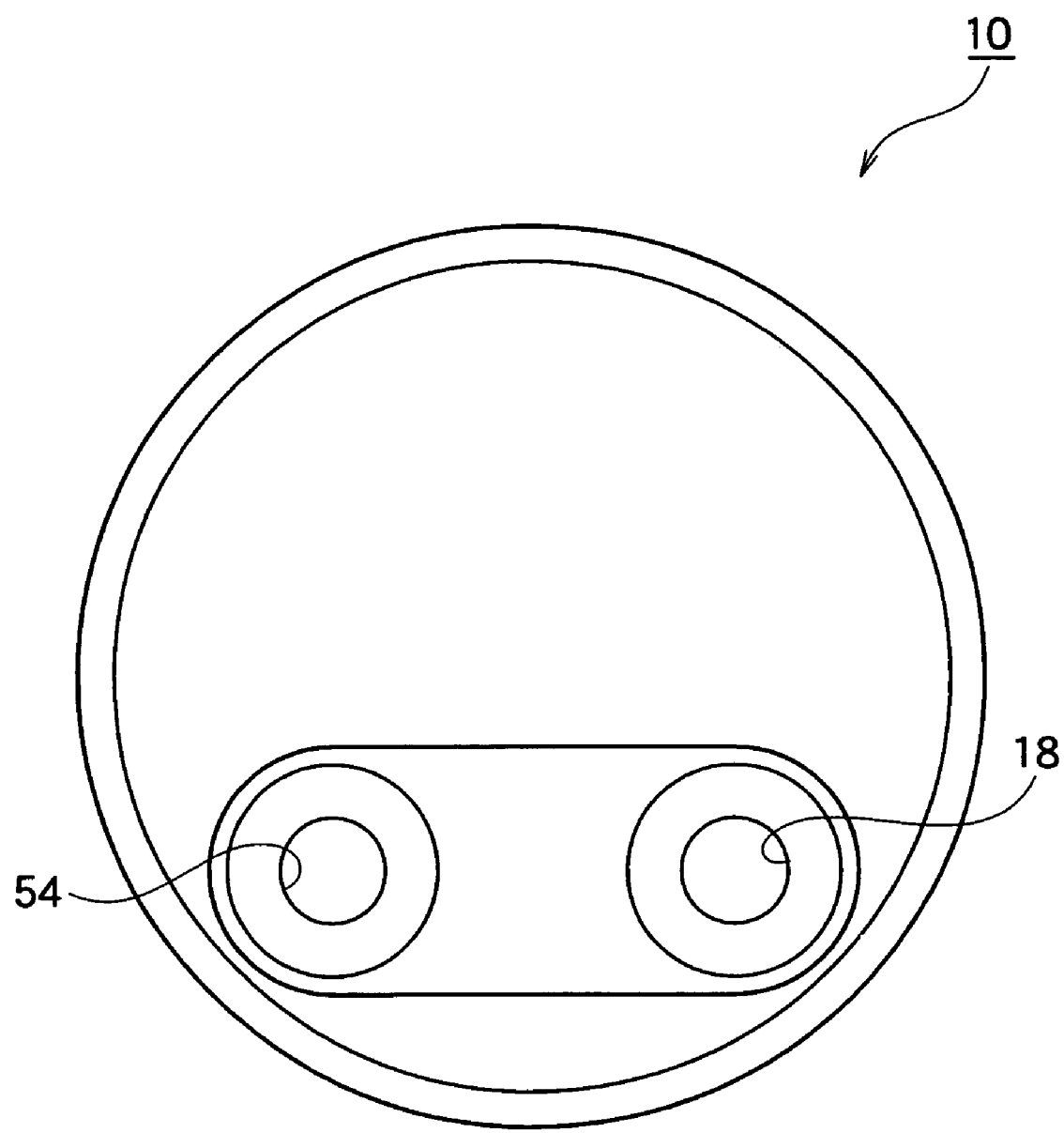
FIG. 3 is a right side view of FIG. 1.
Figure 4:
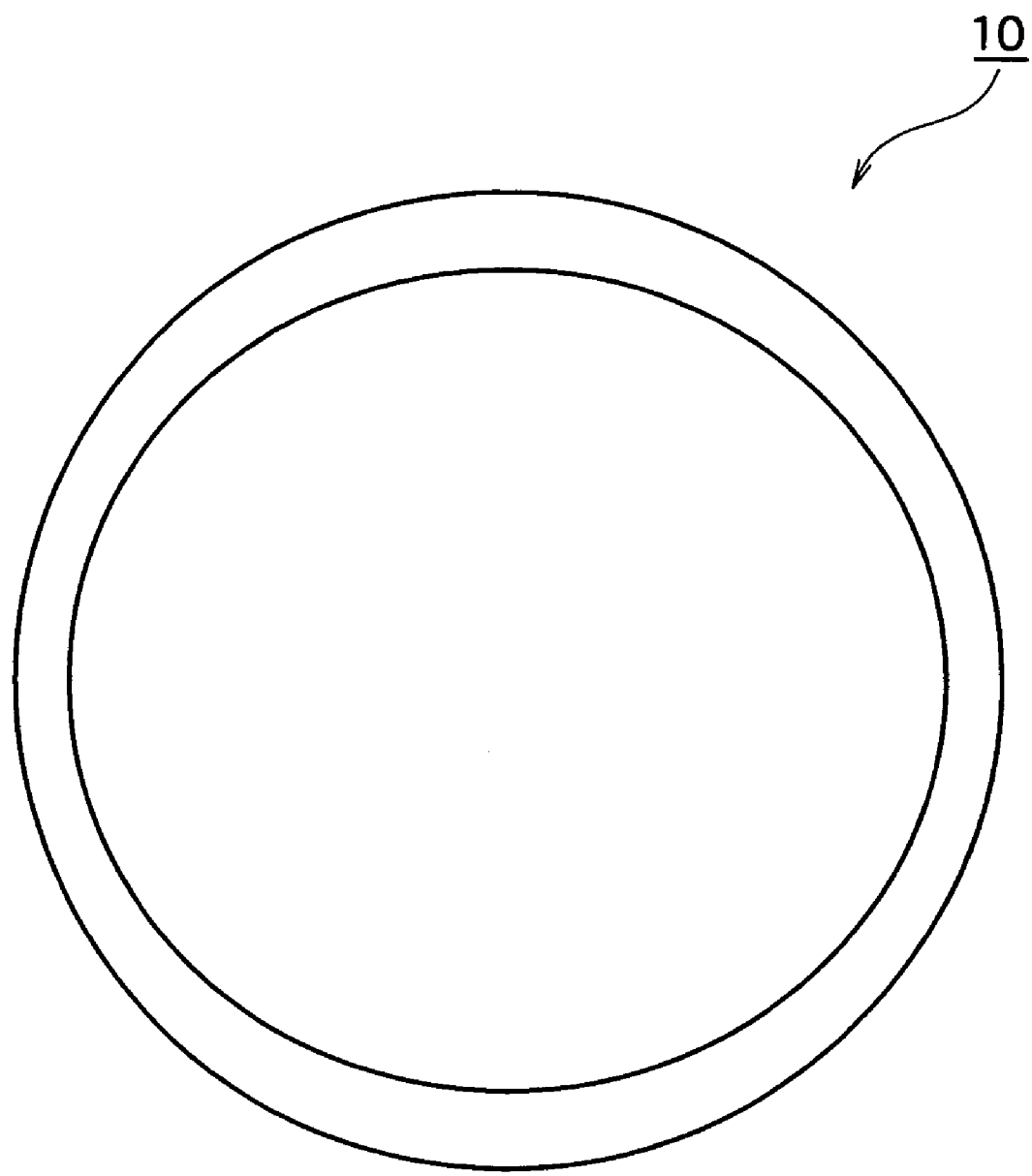
FIG. 4 is a left side view of FIG. 1.

As shown in FIGS. 1 and 2, an apparatus 10 for identifying the concentration of the urea of a urea solution according to the present invention comprises a urea concentration identifying apparatus body 12, and a first passage 14 and a second passage 16 which are formed in the urea concentration identifying apparatus body 12.

As shown in FIG. 1, a urea solution to be identified flows in the direction of the arrows from a urea solution inlet 18 into the first passage 14 passes through an intermediate chamber 56. Then, the urea solution passes through the intermediate chamber 56, and thereafter, enters the second passage 16 to temporarily stay in a urea concentration identifying chamber 20.

The urea concentration identifying chamber 20 is provided with an opening portion 22 for a urea concentration identifying sensor taking the shape of an almost truck in an upper part thereof.

As shown in FIG. 2, a urea concentration identifying sensor 24 is attached to the opening portion 22 for the urea concentration identifying sensor.

Figure 5:
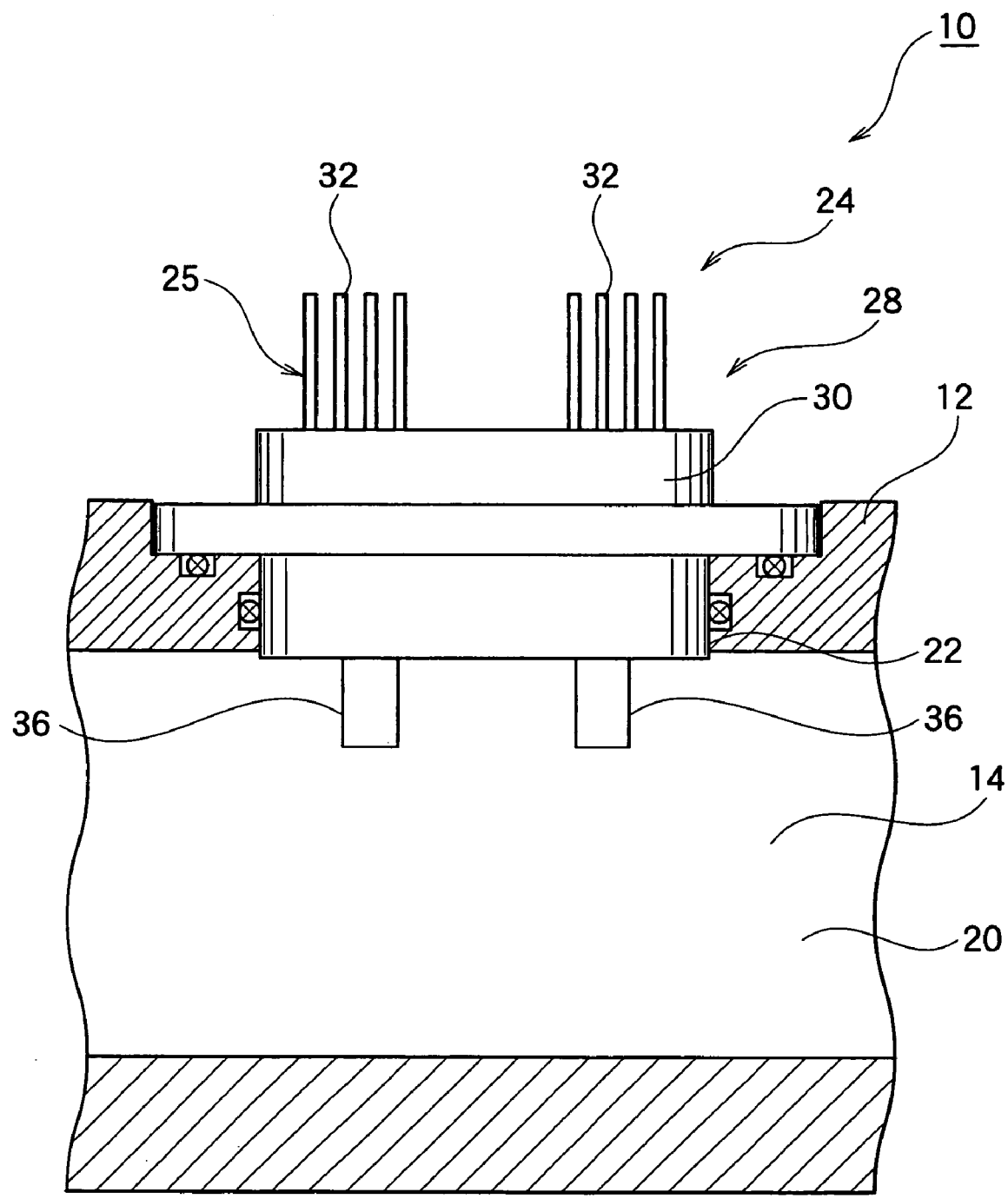
FIG. 5 is a partially enlarged sectional view showing a state in which a urea concentration identifying sensor is attached in FIG. 2.

As shown in FIG. 5, the urea concentration identifying sensor 24 includes a urea concentration identifying sensor heater 25 and a liquid temperature sensor 28 provided apart from the urea concentration identifying sensor heater 25 at a constant interval. Then, the urea concentration identifying sensor heater 25 and the liquid temperature sensor 28 are formed integrally by a mold resin 30.

Figure 6:
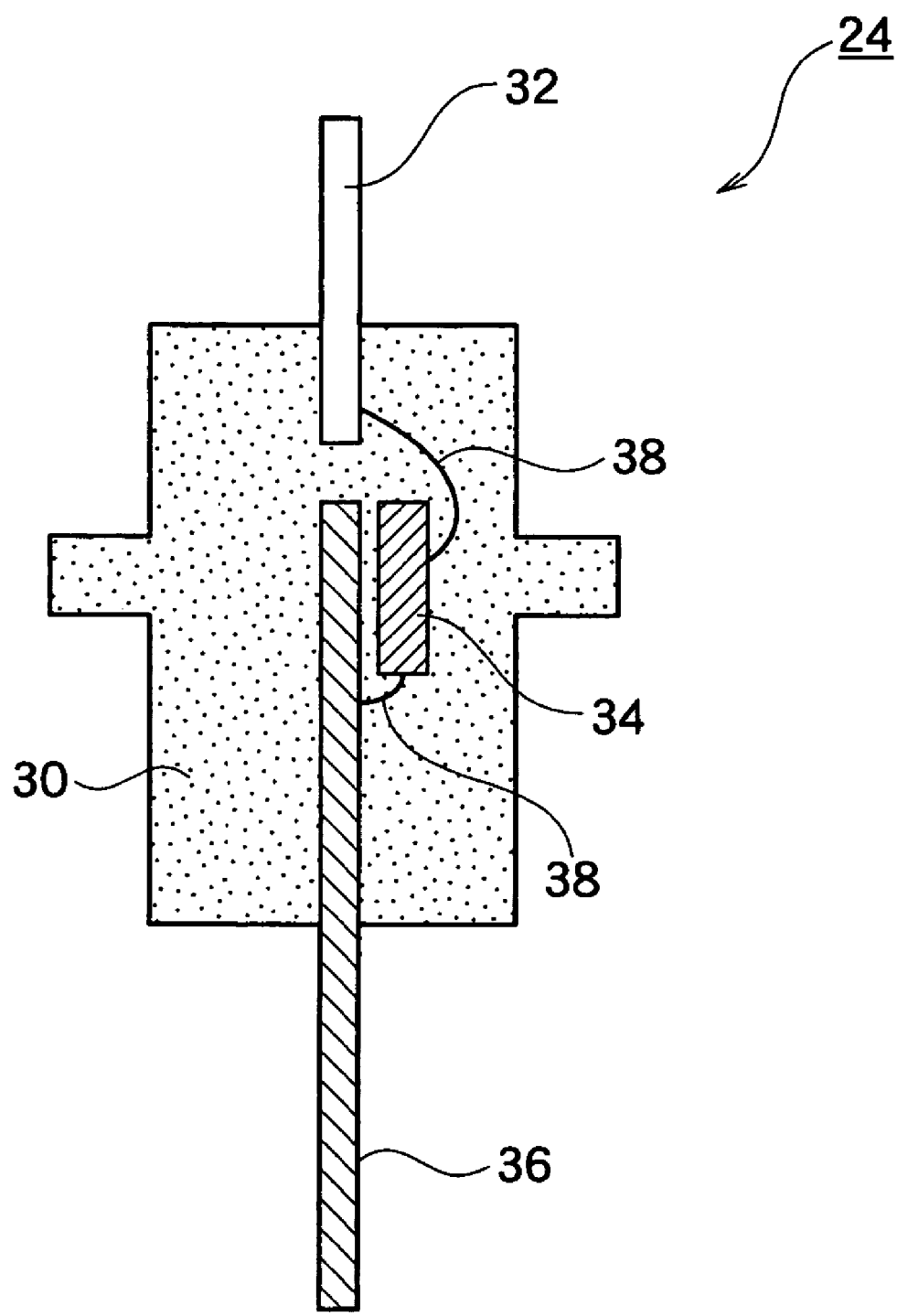
FIG. 6 is a sectional view showing the urea concentration identifying sensor.

As shown in FIG. 6, moreover, the urea concentration identifying sensor heater 25 includes a lead electrode 32 and a thin film chip portion 34. Moreover, the urea concentration identifying sensor heater 25 is provided with a metallic fin 36 protruded into the urea concentration identifying chamber 20 to directly come in contact with the identified urea solution through the opening portion 22 for the urea concentration identifying sensor from the mold resin 30. Then, the lead electrode 32, the thin film chip portion 34 and the fin 36 are mutually connected electrically through a bonding wire 38.

On the other hand, the liquid temperatures sensor 28 also has the same structure as that of the urea concentration identifying sensor heater 25, and includes the lead electrode 32, the thin film chip portion 34, the fin 36 and the bonding wire 38 respectively.

Figure 7:
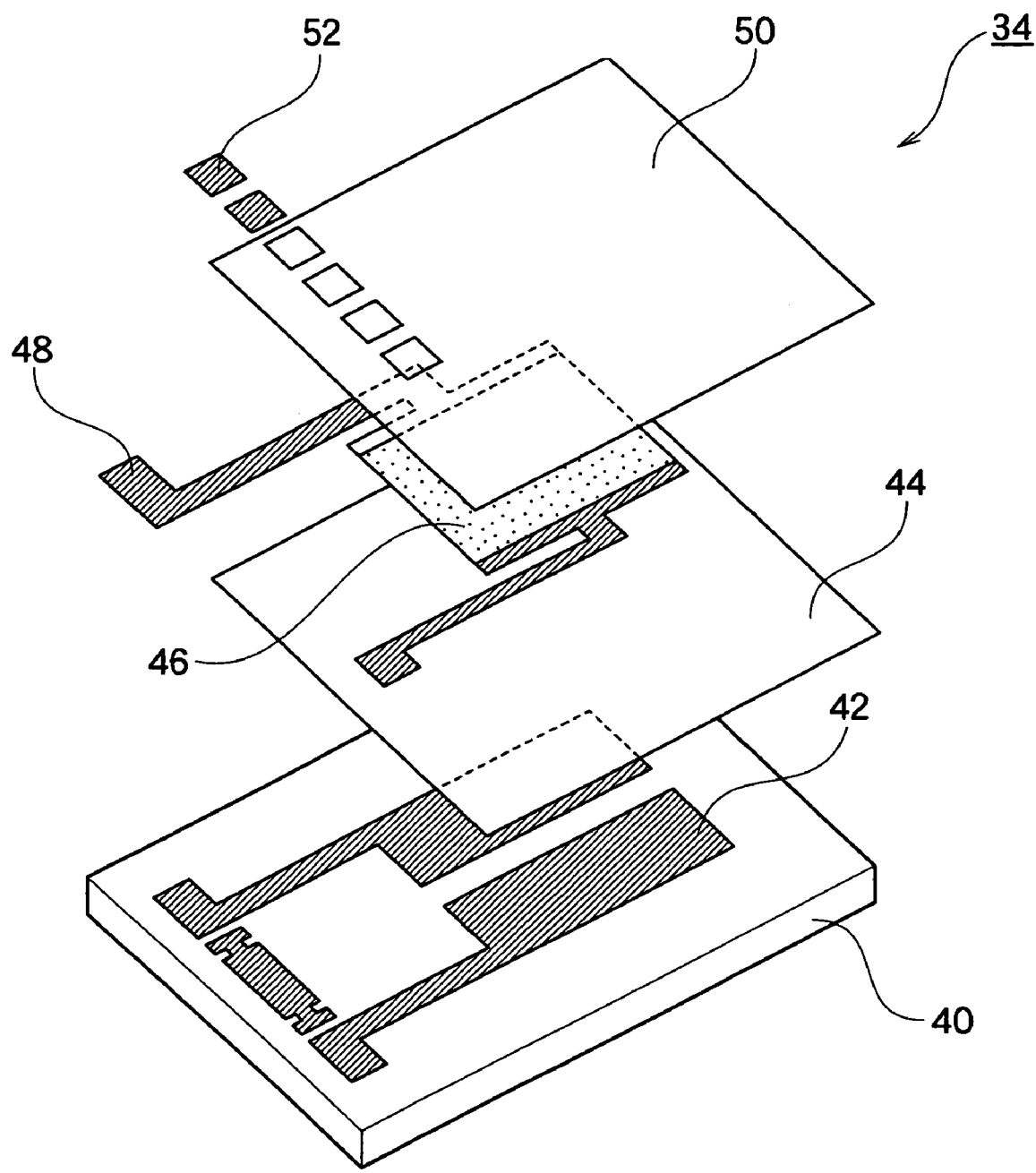
FIG. 7 is a partially enlarged exploded perspective view showing a state in which the thin film chip portions of the urea concentration identifying sensor are laminated.

As shown in FIG. 7, the thin film chip portion 34 is constituted by a thin film-shaped chip in which a substrate 40 formed of $Al_2O_3$, a temperature sensor (temperature detector) 42 formed of PT, an interlayer insulating film 44 formed of $SiO_2$, a heater (heating member) 46 formed of $TaSiO_2$, a heating member electrode 48 formed of Ni, a protective film 50 formed of $SiO_2$, and an electrode pad 52 formed of Ti/Au are provided in order, for example.

While the thin film chip portion 34 of the liquid temperature sensor 28 also has the same structure, it is so constituted as not to cause the heater (heating member) 46 to act but to cause only the temperature sensor (temperature detector) 42 to act.

After the liquid type of the identified urea solution is identified by the urea concentration identifying sensor 24, the identified urea solution is discharged from the urea concentration identifying chamber 20 to an outside through a urea solution discharge port 54.

In FIGS. 1 and 2, moreover, a circuit board member connected to the urea concentration identifying sensor 24 and a lid member for covering the circuit board member are not shown.

Figure 8:
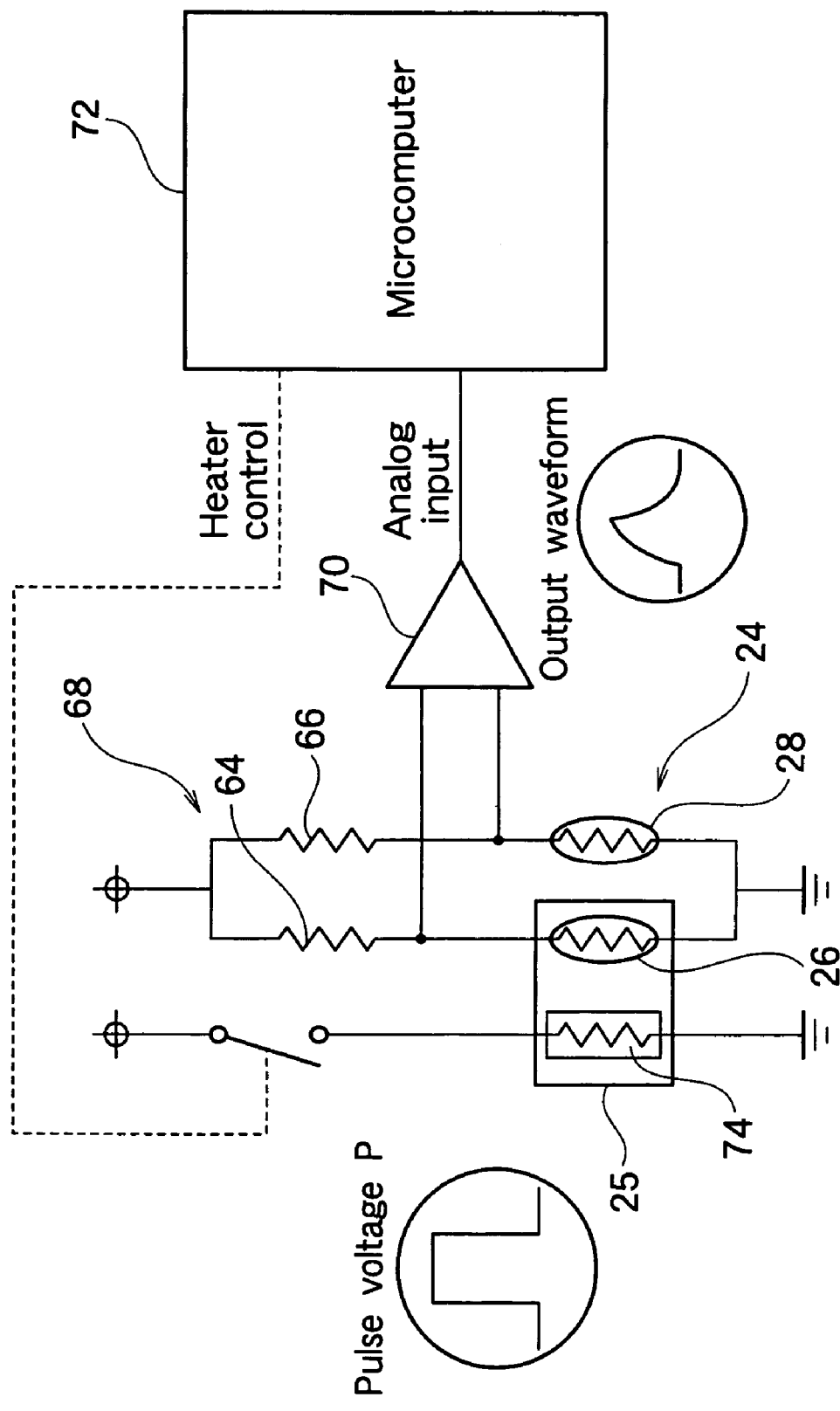
FIG. 8 is a schematic diagram showing the structure of a circuit according to the example of the apparatus for identifying the concentration of the urea of a urea solution according to the present invention.

The apparatus 10 for identifying the concentration of the urea of a urea solution according to the present invention has circuit structure shown in FIG. 8.

In FIG. 8, an identifying liquid temperature sensor 26 of the urea concentration identifying sensor heater 25 and the liquid temperature sensor 28 in the urea concentration identifying sensor 24 are connected to each other through two resistors 64 and 66, thereby constituting a bridge circuit 68. The output of the bridge circuit 68 is connected to the input of an amplifier 70, and the output of the amplifier 70 is connected to the input of a computer 72 constituting an identification control portion.

Moreover, the applied voltage of a heater 74 of the urea concentration identifying sensor heater 25 is controlled by a computer 72.

In the apparatus 10 for identifying the concentration of the urea of a urea solution which has above-described structure, the concentration of the urea of the urea solution is identified in the following manner.

First of all, the identified urea solution is caused to flow from the urea solution inlet 18 of the first passage 14 of the apparatus 10 for identifying the concentration of the urea of a urea solution and is caused to stay temporarily in the urea concentration identifying chamber 20 of the second passage 16.

Figure 9:
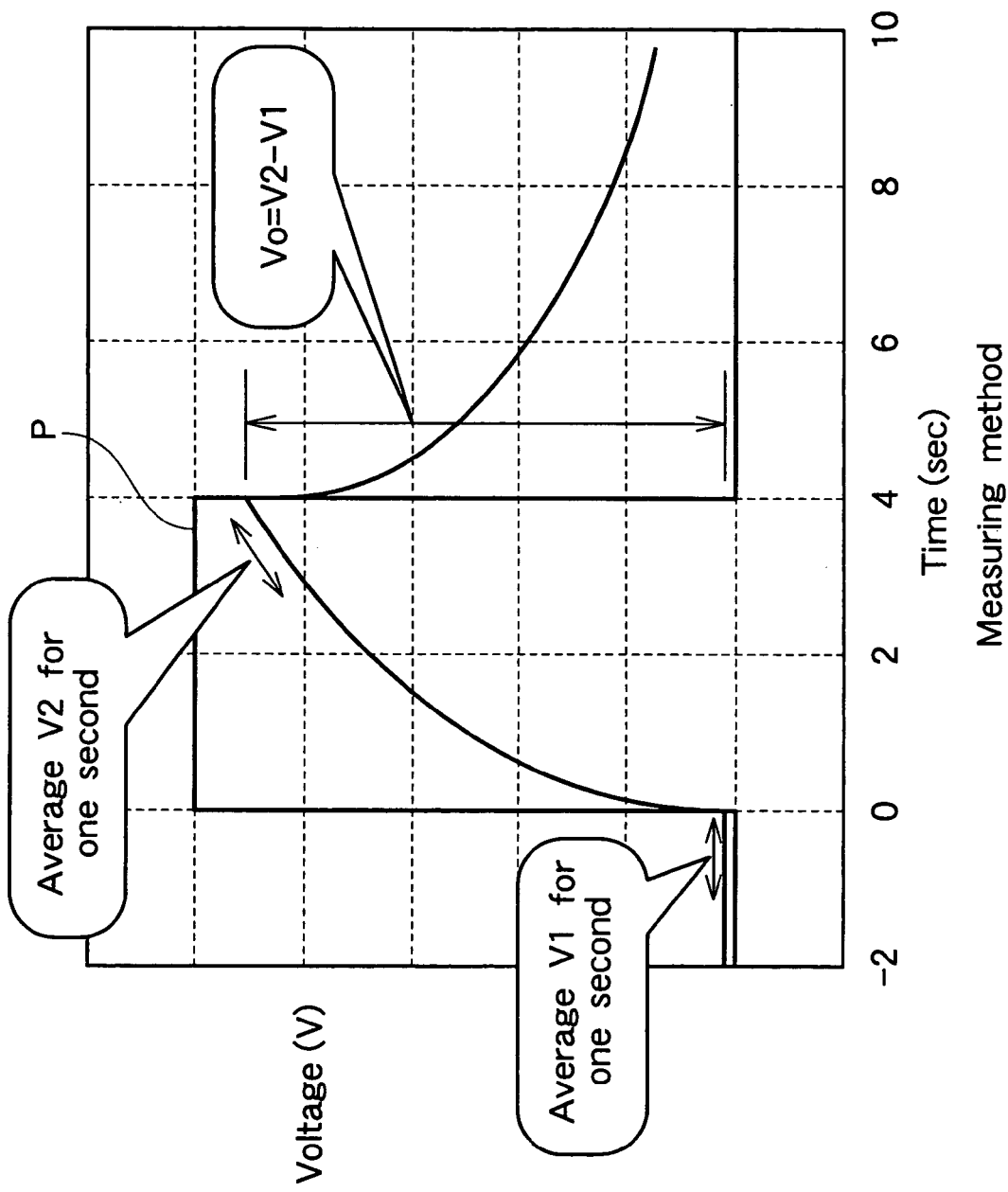
FIG. 9 is a graph showing a relationship between a time and a voltage, illustrating a method for identifying the concentration of a urea using the apparatus for identifying the concentration of the urea of a urea solution according to the present invention.

As shown in FIGS. 8 and 9, a pulse voltage P is applied to the heater 74 of the urea concentration identifying sensor heater 25 under the control of the computer 72 for a predetermined time, that is, four seconds in the present example, and a change in the temperature of the analog output of a sensing portion, that is, the sensor bridge circuit 68 shown in FIG. 8 is measured.

More specifically, as shown in FIG. 9, the voltage difference of the sensor bridge circuit 68 is sampled at a predetermined number of times, for example, 256 times in the present example for one second before the pulse voltage P is applied to the heater 74 of the urea concentration identifying sensor heater 25, and an average value thereof is set to be an average initial voltage V1. The value of the average initial voltage V1 corresponds to the initial temperature of the identifying liquid temperature sensor 26.

As shown in FIG. 9, the predetermined pulse voltage P, that is, a voltage of 10V in the present example is applied to the heater 74 of the urea concentration identifying sensor heater 25 for four seconds. Subsequently, a value obtained by sampling a peak voltage at a predetermined number of times, for example, 256 times in the present example for one second after a predetermined time, for example, 3 seconds in the present example is set to be an average peak voltage V2. The average peak voltage V2 corresponds to the peak temperature of the identifying liquid temperature sensor 26.

A voltage output difference V0 is obtained from a voltage difference between the average initial voltage V1 and the average peak voltage V2, that is, $$V0=V2-V1.$$

Figure 10:
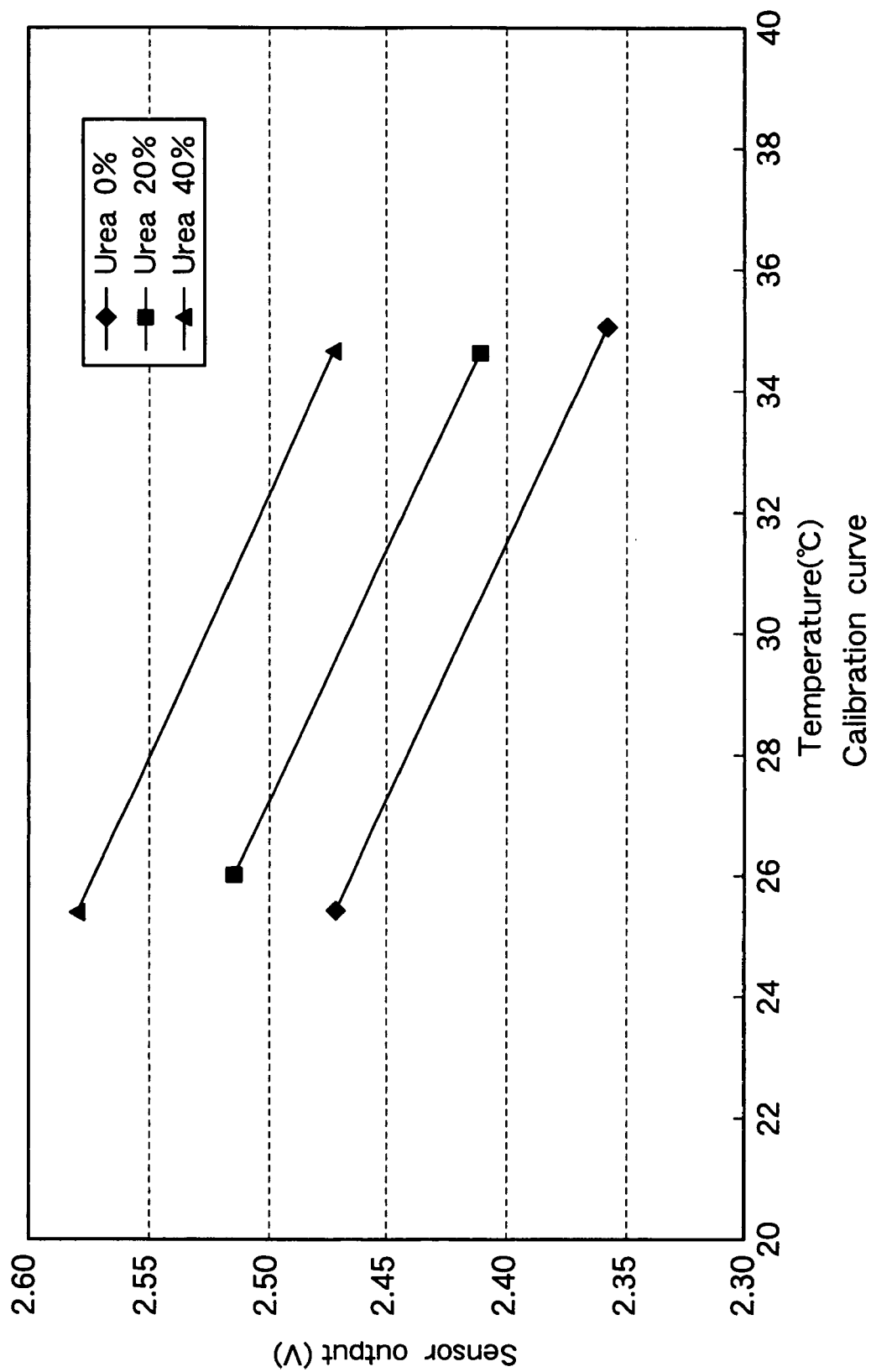
FIG. 10 is a graph showing a calibration curve, illustrating the method for identifying the concentration of a urea using the apparatus for identifying the concentration of the urea of a urea solution according to the present invention.

By such a method, as shown in FIG. 10, calibration curve data to be the correlation of a voltage output difference with a temperature are previously obtained for a predetermined reference urea solution, that is, 0% by weight of urea, 40% by weight of urea and 20% by weight of urea in the present example, and are stored in the computer 72 constituting the identification control portion.

Based on the calibration curve data, a proportional calculation is carried out in the computer 72 and the concentration of the urea of the urea solution is identified with the voltage output difference V0 obtained for the identified urea solution.

More specifically, as shown in FIG. 11, a liquid type voltage output Vout for the voltage output difference V0 at a measuring temperature T of the identified urea solution is correlated with an output voltage for a voltage output difference at a measuring temperature for a predetermined threshold reference urea solution (20% by weight of urea and 40% by weight of urea in the present example) and is thus corrected.

In other words, as shown in FIG. 11(A), a voltage output difference V0–20 of 20% by weight of urea, a voltage output difference V0–40 of 40% by weight of urea and a voltage output difference V0–S of the identified urea solution are obtained at the temperature T based on the calibration curve data.

As shown in FIG. 11(B), the liquid type voltage output Vout of the identified urea solution is obtained by setting the liquid type output of the threshold reference urea solution, so that a correlation with the properties of the urea can be acquired. In this case to have a predetermined voltage, that is, by setting the liquid type output of 40% by weight of urea to be 3.5V and the liquid type output of 20% by weight of urea to be 0.5V in the present example.

The liquid type voltage output Vout of the identified urea solution is previously compared with data stored in the computer 72 based on the calibration curve data. Consequently, it is possible to identify the concentration of the urea of the urea solution accurately and immediately (instantaneously).

The method for identifying the concentration of the urea of a urea solution described above utilizes a natural convection and a principle in which the kinetic viscosity of the urea and the sensor output have a correlation.

FIG. 12 is the same schematic diagram as FIG. 13, illustrating an example in which the apparatus 10 for identifying the concentration of the urea of a urea solution having such a structure is applied to a car system. As used herein, the term "car" includes all types of vehicles and machines which are powered by an internal combustion engine, including automobiles and trucks of all sizes.

The same components as those in FIG. 13 have the same reference numerals and detailed description thereof will be omitted.

In a car system 100, the apparatus 10 for identifying the concentration of the urea of a urea solution is provided in a urea solution tank 132 or on the upstream side of a urea pump 134.

The apparatus 10 for identifying the concentration of the urea of a urea solution identifies the concentration of the urea of the urea solution in the urea solution tank 132 or on the upstream or downstream side of the urea pump 134 (the case of the upstream side will be described in the present example for convenience of explanation) and sets the concentration of the urea to be sprayed onto the upstream side of a catalytic device 116 into a constant state, for example, 32.5% by weight of urea and 67.5% by weight of $H_2O$ in order to efficiently generate a reducing reaction at the upstream side of the catalytic device 116 without causing the urea solution to cake.

Accordingly, the urea of the urea solution in the urea tank can be maintained to have a predetermined concentration. Therefore, it is possible to greatly decrease NOx in an exhaust gas by a reduction.

While the preferred examples of the present invention have been described above, the present invention is not restricted thereto but various changes can be made without departing from the objects of the present invention, for example, a pulse voltage P, the number of sampling operations and the like can be changed properly.

According to the present invention, it is sufficient that a pulse voltage is applied for a predetermined time. Consequently, it is possible to identify the concentration of the urea of a urea solution accurately and immediately through heating for a short time.

More specifically, there are utilized the correlation of the kinetic viscosity of the urea solution with a sensor output, a natural convection, and furthermore, an applied voltage having one pulse. Therefore, it is possible to identify the concentration of the urea of the urea solution accurately and immediately.

According to the present invention, moreover, it is possible to accurately obtain a voltage output difference V0 based on the average value of sampling at a predetermined number of times for the applied voltage having one pulse. Consequently, it is possible to identify the concentration of the urea of the urea solution accurately and immediately.

According to the present invention, furthermore, the concentration of the urea of the urea solution is identified with the voltage output difference V0 obtained for the identified urea solution based on calibration curve data to be the correlation of a voltage output difference with a temperature for a predetermined reference urea solution which is prestored. Therefore, it is possible to identify the concentration of the urea of the urea solution more accurately and immediately.

According to the present invention, moreover, a liquid type voltage output Vout for the voltage output difference V0 at the measuring temperature of the identified urea solution is corrected to be correlated with the output voltage for the voltage output difference at the measuring temperature for a predetermined threshold reference urea solution. Consequently, it is possible to eliminate the influence of the temperature on the voltage output difference V0, thereby giving the correlation of the liquid type voltage output Vout with the properties of the urea solution more accurately. Thus, it is possible to identify the concentration of the urea of the urea solution further accurately and immediately.

According to the present invention, furthermore, a mechanism portion for carrying out a mechanical operation is not present. Therefore, an operation failure is not caused by a deterioration with the passage of time, foreign matters in the urea solution or the like. Thus, it is possible to identify the concentration of the urea of the urea solution accurately and immediately.

In addition, the sensor portion can be constituted to be very small-sized. Consequently, it is possible to identify the concentration of the urea of the urea solution accurately with a very excellent thermal responsiveness.

According to the present invention, moreover, the heater of the urea concentration identifying sensor heater, the identifying liquid temperature sensor and the liquid temperature sensor do not directly come in contact with the identified urea solution. Therefore, an operation failure is not caused by a deterioration with the passage of time, foreign matters in the urea solution or the like. Thus, it is possible to identify the concentration of the urea of the urea solution accurately and immediately.

According to the present invention, furthermore, it is possible to accurately and immediately decide whether or not 32.5% by weight of urea and 67.5% by weight of $H_2O$ are set in order to efficiently generate a reducing reaction at the upstream side of the catalytic device 116 without causing the urea solution to cake.

Accordingly, the urea of the urea solution in the urea tank can be maintained to have a predetermined concentration. Consequently, the NOx in the exhaust gas can be greatly decreased by a reduction. Thus, the present invention can produce various remarkable and peculiar functions and effects, which is very excellent.

The invention claimed is:

1. An apparatus for identifying a concentration of a urea of a urea solution, comprising:
   a urea concentration identifying chamber for causing an identified urea solution introduced into a urea concentration identifying apparatus body to stay temporarily;
   a urea concentration identifying sensor heater provided in the urea concentration identifying chamber; and
   a liquid temperature sensor provided in the urea concentration identifying chamber apart from the urea concentration identifying sensor heater at a constant interval;
   the urea concentration identifying sensor heater including a heater and an identifying liquid temperature sensor provided in the vicinity of the heater, and
   an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor,
   wherein the liquid temperature sensor is constituted to come in contact with the identified urea solution through a fin.

2. An apparatus for identifying a concentration of a urea of a urea solution, comprising:
   a urea concentration identifying chamber for causing an identified urea solution introduced into a urea concentration identifying apparatus body to stay temporarily;
   a urea concentration identifying sensor heater provided in the urea concentration identifying chamber; and
   a liquid temperature sensor provided in the urea concentration identifying chamber apart from the urea concentration identifying sensor heater at a constant interval;
   the urea concentration identifying sensor heater including a heater and an identifying liquid temperature sensor provided in the vicinity of the heater, and
   an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $V0=V2-V1$, wherein the heater and the identifying liquid temperature sensor in the urea concentration identifying sensor heater are constituted to come in contact with the identified urea solution through a fin, respectively.

3. An apparatus for identifying a concentration of a urea of a urea solution, comprising:
   a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the identification control portion identifies a concentration of a urea of a urea solution with the voltage output difference V0 obtained for the identified urea solution based on calibration curve data to be a correlation of a voltage output difference with a temperature for a predetermined reference urea solution prestored in the identification control portion, wherein the heater and the identifying liquid temperature sensor in the urea concentration identifying sensor heater are constituted to come in contact with the identified urea solution through a fin, respectively.

4. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the identification control portion correlates a liquid type voltage output Vout for the voltage output difference V0 at a measuring temperature of the identified urea solution with an output voltage for a voltage output difference at a measuring temperature for a predetermined threshold reference urea solution and thus carries out a correction, wherein the heater and the identifying liquid temperature sensor in the urea concentration identifying sensor heater are constituted to come in contact with the identified urea solution through a fin, respectively.

5. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the urea concentration identifying sensor heater is a laminated urea concentration identifying sensor heater in which a heater and an identifying liquid temperature sensor are laminated through an insulating layer, and wherein the heater and the identifying liquid temperature sensor in the urea concentration identifying sensor heater are constituted to come in contact with the identified urea solution through a fin, respectively.

6. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0 = V2 - V1,$$

wherein the liquid temperature sensor is constituted to come in contact with the identified urea solution through a fin.

7. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the identification control portion identifies a concentration of a urea of a urea solution with the voltage output difference V0 obtained for the identified urea solution based on calibration curve data to be a correlation of a voltage output difference with a temperature for a predetermined reference urea solution prestored in the identification control portion, and wherein the liquid temperature sensor is constituted to come in contact with the identified urea solution through a fin.

8. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the identification control portion correlates a liquid type voltage output Vout for the voltage output difference V0 at a measuring temperature of the identified urea solution with an output voltage for a voltage output difference at a measuring temperature for a predetermined threshold reference urea solution and thus carries out a correction, and wherein the liquid temperature sensor is constituted to come in contact with the identified urea solution through a fin.

9. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference V0 corresponding to a temperature difference between an initial temperature and a peak temperature in the identifying liquid temperature sensor, wherein the urea concentration identifying sensor heater is a laminated urea concentration identifying sensor heater in which a heater and an identifying liquid temperature sensor are laminated through an insulating layer, and wherein the liquid temperature sensor is constituted to come in contact with the identified urea solution through a fin.

10. An apparatus for identifying a concentration of a urea of a urea solution, comprising:

a urea concentration identifying chamber for causing an identified urea solution introduced into a urea concentration identifying apparatus body to stay temporarily when identifying a concentration of a urea;

a urea concentration identifying sensor heater provided in the urea concentration identifying chamber; and an identification control portion for applying a pulse voltage to the urea concentration identifying sensor heater for a predetermined time, for heating the identified urea solution staying temporarily in the urea concentration identifying chamber by the urea concentration identifying sensor heater, and for identifying the concentration of the urea with a voltage output difference V0 corresponding to a temperature difference between an initial temperature and a peak temperature in the urea concentration identifying sensor heater, wherein the heater and the identifying liquid temperature sensor in the urea concentration identifying sensor heater are constituted to come in contact with the identified urea solution through a fin, respectively.

11. An apparatus for identifying a concentration of a urea of a urea solution, comprising:

a urea concentration identifying chamber for causing an identified urea solution introduced into a urea concentration identifying apparatus body to stay temporarily when identifying a concentration of a urea;

a urea concentration identifying sensor heater provided in the urea concentration identifying chamber; and an identification control portion for applying a pulse voltage to the urea concentration identifying sensor heater for a predetermined time, for heating the identified urea solution staying temporarily in the urea concentration identifying chamber by the urea concentration identifying sensor heater, and for identifying the concentration of the urea with a voltage output difference V0 corresponding to a temperature difference between an initial temperature and a peak temperature in the urea concentration identifying sensor heater, wherein the liquid temperature sensor is constituted to come in contact with the identified urea solution through a fin.

12. An apparatus for identifying a concentration of a urea of a urea solution, comprising:

a urea concentration identifying chamber for causing an identified urea solution introduced into a urea concentration identifying apparatus body to stay temporarily when identifying a concentration of a urea;

a urea concentration identifying sensor heater provided in the urea concentration identifying chamber; and an identification control portion for applying a pulse voltage to the urea concentration identifying sensor heater for a predetermined time, for heating the identified urea solution staying temporarily in the urea concentration identifying chamber by the urea concentration identifying sensor heater, and for identifying the concentration of the urea with a voltage output difference VO corresponding to a temperature difference between an initial temperature and a peak temperature in the urea concentration identifying sensor heater, wherein the urea concentration identifying sensor heater is constituted to come in contact with the identified urea solution through a fin.

13. An apparatus for identifying a concentration of a urea of a urea solution, comprising:

a urea concentration identifying chamber for causing an identified urea solution introduced into a urea concentration identifying apparatus body to stay temporarily when identifying a concentration of a urea;

a urea concentration identifying sensor heater provided in the urea concentration identifying chamber; and an identification control portion for applying a pulse voltage to the urea concentration identifying sensor heater for a predetermined time, for heating the identified urea solution staying temporarily in the urea concentration identifying chamber by the urea concentration identifying sensor heater, and for identifying the concentration of the urea with a voltage output difference $V0$ corresponding to a temperature difference between an initial temperature and a peak temperature in the urea concentration identifying sensor heater, wherein the urea concentration identifying sensor heater is constituted to come in contact with the identified urea solution through a fin.

14. The apparatus for identifying a concentration of a urea of a urea solution according to claim 13, wherein the voltage output difference $V0$ is equal to a voltage difference between an average initial voltage $V1$ obtained by sampling an initial voltage before application of the pulse voltage at a predetermined number of times and an average peak voltage $V2$ obtained by sampling a peak voltage after the application of the pulse voltage at a predetermined number of times, that is, $$V0 = V2 - V1.$$

15. The apparatus for identifying a concentration of a urea of a urea solution according to claim 13, wherein the identification control portion identifies a concentration of a urea of a urea solution with the voltage output difference $V0$ obtained for the identified urea solution based on calibration curve data to be a correlation of a voltage output difference with a temperature for a predetermined reference urea solution pre-stored in the identification control portion.

16. The apparatus for identifying a concentration of a urea of a urea solution according to claim 13, wherein the identification control portion correlates a liquid type voltage output Vout for the voltage output difference $V0$ at a measuring temperature of the identified urea solution with an output voltage for a voltage output difference at a measuring temperature for a predetermined threshold reference urea solution and thus carries out a correction.

17. The apparatus for identifying a concentration of a urea of a urea solution according to claim 13, wherein the urea concentration identifying sensor heater is a laminated urea concentration identifying sensor heater in which a heater and an identifying liquid temperature sensor are laminated through an insulating layer.

18. An apparatus for identifying a concentration of a urea of a urea solution, comprising:

a urea concentration identifying chamber for causing an identified urea solution introduced into a urea concentration identifying apparatus body to stay temporarily;

a urea concentration identifying sensor heater provided in the urea concentration identifying chamber; and a liquid temperature sensor provided in the urea concentration identifying chamber apart from the urea concentration identifying sensor heater at a constant interval;

the urea concentration identifying sensor heater including a heater and an identifying liquid temperature sensor provided in the vicinity of the heater, and the apparatus further comprising an identification control portion for applying a pulse voltage to the urea concentration identifying sensor heater for a predetermined time, heating the identified urea solution staying temporarily in the urea concentration identifying chamber by the heater and identifying the concentration of the urea with a voltage output difference $V0$ corresponding to a temperature difference between an initial temperature and a peak temperature in the identifying liquid temperature sensor, wherein the heater and the identifying liquid temperature sensor in the urea concentration identifying sensor heater are constituted to come in contact with the identified urea solution through a fin, respectively.

19. The apparatus for identifying a concentration of a urea of a urea solution according to claim 18, wherein the urea concentration identifying sensor heater is a laminated urea concentration identifying sensor heater in which a heater and an identifying liquid temperature sensor are laminated through an insulating layer.

20. The apparatus for identifying a concentration of a urea of a urea solution according to claim 18, wherein the identification control portion correlates a liquid type voltage output Vout for the voltage output difference $V0$ at a measuring temperature of the identified urea solution with an output voltage for a voltage output difference at a measuring temperature for a predetermined threshold reference urea solution and thus carries out a correction.

21. The apparatus for identifying a concentration of a urea of a urea solution according to claim 20, wherein the urea concentration identifying sensor heater is a laminated urea concentration identifying sensor heater in which a heater and an identifying liquid temperature sensor are laminated through an insulating layer.

22. The apparatus for identifying a concentration of a urea of a urea solution according to claim 18, wherein the identification control portion identifies a concentration of a urea of a urea solution with the voltage output difference $V0$ obtained for the identified urea solution based on calibration curve data to be a correlation of a voltage output difference with a temperature for a predetermined reference urea solution pre-stored in the identification control portion.

23. The apparatus for identifying a concentration of a urea of a urea solution according to claim 22, wherein the identification control portion correlates a liquid type voltage output Vout for the voltage output difference $V0$ at a measuring temperature of the identified urea solution with an output voltage for a voltage output difference at a measuring temperature for a predetermined threshold reference urea solution and thus carries out a correction.

24. The apparatus for identifying a concentration of a urea of a urea solution according to claim 22, wherein the urea concentration identifying sensor heater is a laminated urea concentration identifying sensor heater in which a heater and an identifying liquid temperature sensor are laminated through an insulating layer.

25. The apparatus for identifying a concentration of a urea of a urea solution according to claim 18, wherein the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0=V2-V1.$$

26. The apparatus for identifying a concentration of a urea of a urea solution according to claim 25, wherein the identification control portion identifies a concentration of a urea of a urea solution with the voltage output difference V0 obtained for the identified urea solution based on calibration curve data to be a correlation of a voltage output difference with a temperature for a predetermined reference urea solution pre-stored in the identification control portion.

27. The apparatus for identifying a concentration of a urea of a urea solution according to claim 25, wherein the identification control portion correlates a liquid type voltage output Vout for the voltage output difference V0 at a measuring temperature of the identified urea solution with an output voltage for a voltage output difference at a measuring temperature for a predetermined threshold reference urea solution and thus carries out a correction.

28. The apparatus for identifying a concentration of a urea of a urea solution according to claim 25, wherein the urea concentration identifying sensor heater is a laminated urea concentration identifying sensor heater in which a heater and an identifying liquid temperature sensor are laminated through an insulating layer.

* * * * *

UNITED STATES PATENT AND TRADEMARK OFFICE
CERTIFICATE OF CORRECTION

| | |
|---|---|
| PATENT NO. | : 7,971,425 B2 |
| APPLICATION NO. | : 10/527255 |
| DATED | : July 5, 2011 |
| INVENTOR(S) | : Takahata et al. |

Page 1 of 1

It is certified that error appears in the above-identified patent and that said Letters Patent is hereby corrected as shown below:

In the Title, line 2, "Indentifying" should read --Identifying--

Claim 9, col. 14, line 10, "VO" should read --V0--

Claim 11, col. 14, lines 57-60, the text beginning with "wherein the liquid" should begin a separate and final paragraph Signed and Sealed this
Fifteenth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,971,425 B2 | Page 1 of 1 |
| APPLICATION NO. | : 10/527255 | |
| DATED | : July 5, 2011 | |
| INVENTOR(S) | : Takahata et al. | |

It is certified that error appears in the above-identified patent and that said Letters Patent is hereby corrected as shown below:

Title Page, Item (54) and at Column 1, line 2,
<u>In the Title</u>, "Indentifying" should read --Identifying--

<u>Claim 9</u>, col. 14, line 10, "VO" should read --V0--

<u>Claim 11</u>, col. 14, lines 57-60, the text beginning with "wherein the liquid" should begin a separate and final paragraph This certificate supersedes the Certificate of Correction issued November 15, 2011.

Signed and Sealed this
Twentieth Day of December, 2011

David J. Kappos
*Director of the United States Patent and Trademark Office*